United States Patent [19]

Shaw et al.

[11] Patent Number: 5,002,651

[45] Date of Patent: Mar. 26, 1991

[54] MODIFIED MICROELECTRODES WITH RENEWABLE SURFACE AND METHOD OF MAKING SAME

[75] Inventors: Brenda R. Shaw; Kenneth E. Creasy, both of Storrs, Conn.

[73] Assignee: University of Connecticut, Storrs, Conn.

[21] Appl. No.: 319,984

[22] Filed: Mar. 7, 1989

[51] Int. Cl.$^5$ ............................................. C25B 11/00
[52] U.S. Cl. .................................. 204/290 R; 204/291; 204/292; 204/294; 429/42; 429/43; 427/58; 427/113; 427/355
[58] Field of Search ............ 204/290 R, 291; 429/42, 429/43; 427/58, 113, 355

[56] References Cited

U.S. PATENT DOCUMENTS

| | | | |
|---|---|---|---|
| 3,385,780 | 5/1968 | Feng | 204/294 |
| 4,278,525 | 7/1981 | Gestaut | 204/294 |
| 4,337,140 | 6/1982 | Solomon | 204/294 |
| 4,339,322 | 7/1982 | Balko et al. | 204/294 |
| 4,343,767 | 8/1982 | Long et al. | 204/294 |
| 4,472,257 | 9/1984 | Sklyarov et al. | 204/294 |
| 4,510,214 | 4/1985 | Crouse et al. | 429/43 |

FOREIGN PATENT DOCUMENTS

| | | | |
|---|---|---|---|
| 1151108 | 8/1983 | Canada | |
| 4541003 | 12/1970 | Japan | 204/294 |
| 0032368 | 2/1983 | Japan | 429/43 |

OTHER PUBLICATIONS

H. L. Dickstein, "Preparation of Carbon Black-Polymer Composites", University of Mass. Ph. D. Thesis, 1987.
J. Chang, et al, "Electro-Copolymerization of Acrylonitrile and Methyl Acrylate onto Graphite Fibers", Journal of Applied Polymer Science, vol. 34, 2105-2124 (1987).
R. V. Subramanian et al, "Electrodeposition of a Polymer Interphase in Carbon-Fiber Composites", Polymer Composites, Aug. 1986, vol. 7, No. 4, pp. 201-218.
R. V. Bramanian et al, "Electropolymerization on Graphite Fibers", Polymer Engineering Science, May 1978, vol. 18, No. 7, pp. 590-600 (1978).
J. Golas et al, "Carbon-Fiber Micro-Electrodes as Substrates for Mercury Films", Analytica Chimica Acta, 186 (1986), pp. 1-9.
Fathalla Belal et al, "Flow Injection Alalysis of Three N-Substituted Phenothiazine Drugs with Amperometric Detection at a Carbon Fibre-Array Electrode", Analyst, Dec. 1985, vol. 110, pp. 1493-1496.
Lipka et al, "The Electrochemical Behavior of Graphite Fiber-Epoxy Composite Electrodes Containing Varying Fiber Orientations", Electrochemical Science and Technology, Feb. 1988, pp. 368-372.
Neal Sleszynski et al, "Arrays of Very Small Voltammetric Electrodes Based on Reticulated Vitreous Carbon", Analytical Chemistry, vol. 56, No. 2, Feb. 1984, pp. 130-135.
C. Amatore et al., "Charge Transfer at Partially Blocked Surfaces, A Model for the Case of Microscopic (List continued on next page.)

Primary Examiner—John F. Niebling
Assistant Examiner—Kathryn Gorgos

[57] ABSTRACT

Renewable composite microelectrodes for electrochemical applications are formed by an initial coating on an elongated conductive substrate of less than 500 micrometers over at least a portion of its length with a modifier composition, and a superposed coating of electronically resistive polymer. The initial coating is exposed only at the tip portion of the microelectrode. The initial coating may be an absorbed layer of the modifier, a homogeneous layer of a polymeric matrix with the modifier dispersed therein, or a layer of a polymer with a modifier in its chain. The modifier provides distinctive properties to the surface of the electrode which may be electroactivity, inclusion, acidic/basic, complexing/chelating or electrocatalysis. The microelectrode will normally be used with only the tip portion thereof immersed in the solution, and it may be renewed by removing the contaminated tip portion.

36 Claims, 1 Drawing Sheet

OTHER PUBLICATIONS

Active and Inactive Sites", J. Electroanal Chemistry, #147, 1983, pp. 39–51.

Duane Welsshaar et al, "Kel-F-Graphite Composite Electrode as an Electrochemical Detector for Liquid Chromatography and Application to Phenolic Compounds", Alalytical Chemistry, 1981, #53, pp. 1809–1813.

J. Redepenning, "Chemically Modified Electrodes: A General Overview Trends in Analytical Chemistry", vol. 6, No. 1, 1987, pp. 18–22.

L. Santos, et al, "Electrochemistry and Chromatographic Detection of Monosaccharides, Disaccharides, and Related Compounds at an Electrocatalytic Chemically Modified Electrode", Analytica Chimica Acta, 206 (1988), pp. 85–96.

MODIFIED MICROELECTRODES WITH RENEWABLE SURFACE AND METHOD OF MAKING SAME

BACKGROUND OF THE INVENTION

The present invention relates to renewable modified microelectrodes for electrochemical applications and to methods for making same.

Modified electrodes have become of great interest because of their ability to extend the range of characteristics provided by the intrinsic interfacial properties of traditional electrodes. Such electrodes have become important tools in electroanalytical chemistry and the uses have been expanding as new modifiers have been identified.

Heretofore, such electrodes have been prepared by application to the surface of an electrode a coating of a modifier to provide the desired alteration of the surface characteristics. In many applications, the surface layer becomes contaminated or attacked by the solution in which the electrode is immersed so that the modified electrode may not be reused. Moreover, the coating may not be uniform and thus produce variation in activity over the surface of the electrode.

Microelectrodes and ultramicroelectrodes are desirable for many analytical applications. Fabrication of microelectrodes with electroactive surfaces presents substantial problems. Moreover, such microelectrodes become contaminated and require frequent replacement Thus, substitution of another microelectrode may involve some change in microelectrode characteristics and introduce problems of reproducibility of results.

It is an object of the present invention to provide a novel modified electrode which may be renewed by removing a surface portion thereof.

It is also an object to provide such a microelectrode which has substantially uniform characteristics along its length so that it may be renewed by removing end portions and provide substantially similar results.

A further object is to provide an electrode assembly which may combine therein microelectrodes having different types of modification.

Another object is to provide a novel method for preparing modified microelectrodes and for renewing such microelectrodes.

SUMMARY OF THE INVENTION

It has now been found that the foregoing and related objects and advantages may be readily attained in a renewable composite microelectrode for electrochemical which has at least one elongated conductive substrate having a cross section of less than 500 micrometers and selected from the group of conductive fibers and metallic wires. It has disposed upon the substrate an initial coating containing a modifier providing to the electrode distinctive properties which are selected from the group consisting of electroactivity, inclusion, adsorption acidic/basic, complexing/chelating and electrocatalysis. This coating is selected from the group consisting of an adsorbed layer of the modifier, a homogeneous layer of 1-99 percent by weight of a polymeric matrix and 1-99 percent by weight of the modifier dispersed thereon, and a polymer having the modifier in the polymer chain. The electrode also has an electronically resistive polymer coating superposed thereon, but the tip of the electrode is free from the resistive coating. The electrode is renewable by removing a portion thereof to expose a fresh portion of the initial coating at the tip.

Preferably, the substrate is a conductive fiber and the initial and resistive coatings extend over substantially the entire length of the substrate.

The initial coating may comprise a non-conductive polymer having the modifier in the polymer chain, and the modifier may be copolymerizable with a polymerizable monomer to form the non-conductive polymer.

The coating may be a homogeneous layer of a polymeric matrix with the modifier dispersed therein.

The modifier exhibiting electroactive properties are selected from the group consisting of organic compounds, polymers, alloys and metallic compounds.

In the method of making renewable composite microelectrodes, an elongated conductive substrate is selected which has a cross section of less than 500 micrometers and which may be conductive fibers and wires. An initial surface coating is provided along at least a portion of the length of the substrate to form the electrode, and this coating contains a modifier providing to the electrode distinctive properties selected from the group consisting of electroactivity, inclusion, adsorption and electrocatalysis. This coating may be formed by a process selected from the group consisting of absorbing the modifier onto the substrate, and coating the substrate with a homogeneous layer of 1-99 percent by weight of a polymeric matrix and 1-99 percent by weight of the modifier dispersed therein. It may also be formed by coating the substrate with a non-conductive polymer having the modifier in the polymer chain. Subsequently, there is superposed on the initial coating an electronically resistive polymer coating, and the initial coating is exposed at the tip of the substrate.

Optionally, there are included the additional steps of selecting a multiplicity of such microelectrodes having different coatings exhibiting different electroactive properties and assembling such microelectrodes into a composite electrode providing more than one of the properties.

DETAILED DESCRIPTION OF THE INVENTION

The microelectrodes of the present invention utilize an elongated conductive substrate, an initial deposit or coating thereon containing the modifier having the desired electroactive property, and an outer coating of an electronically resistive polymer. However, the end of the microelectrode has the modifier layer exposed for contact with the solution in which the electrode is immersed.

Figure 1:
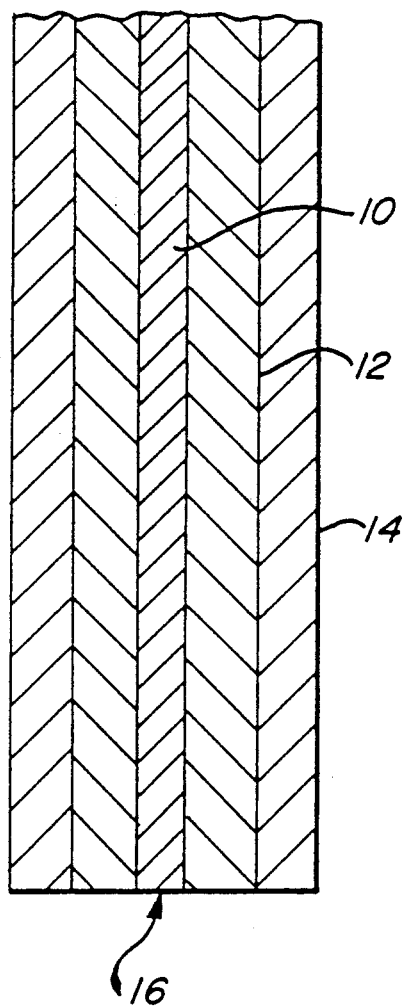
FIG. 1 is a vertical cross section of a microelectrode embodying the present invention.
Figure 2:
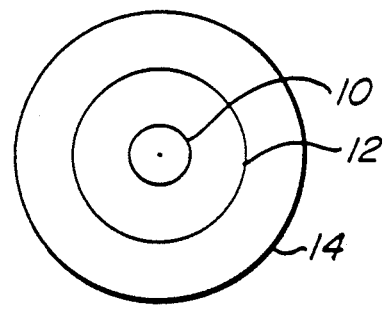
FIG. 2 is a plan view of the tip of the microelectrode of FIG. 1.

As seen in FIGS. 1 and 2, a microelectrode embodying the present invention has an elongated fiber or wire 10 providing a substrate upon which there is deposited an initial surface coating 12 containing the modifier and an outer electronically resistive polymer coating 14. The tip 16 of the initially produced structure is cut off to expose the annular layer of the initial surface coating 12 for contact with the solution in which the electrode is placed over the polymer coating 14 while the rest of the initial surface coating 12 limits such contact to the tip 16.

Figure 3:
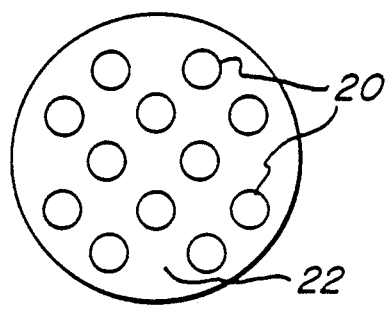
FIG. 3 is a plan view of the tip of a composite electrode produced in accordance with the present invention.

In FIG. 3, a composite electrode is produced by encasing a multiplicity of microelectrodes 20 in a body 22 of electronically resistive ploymer and removing the tip of this composite to expose the surface coating of the individual microelectrodes 20 at the tip.

The conductive substrate may be conductive fibers of graphite or the like, or fine metallic wires. Generally, the substrate will have a diameter of less than 500 micrometers and preferably about 5-100 micrometers. The length will be determined by the desired length for the microelectrode. For some applications, the conductive fiber may be a semi-conductor, i.e., one which exhibits conductivity only at certain applied potential or temperatures. "Conductive" is meant to include the use of such semi-conductors as fibers in electrodes for such special applications.

The outer polymer coating should be one which will electronically insulate the portion of the electrode thereunder and desirable provide structural strength for handling and relative resistance to attack by the solutions in which immersed. Exemplary materials are vinyl polymers such as styrene and acrolites, epoxy polymers, and polychlorotrifluoroethylene polymers. This coating may have a thickness of at least 0.1 nanometers to 5 millimeters, and is preferably about 0.01-10 micrometers.

As previously indicated, the outer coating may encapsulate a multiplicity of conductive substrates having the same or different modifiers in an initial coating thereof. Thus, a microelectrode array may be provided on a single microelectrode assembly.

The initial coating of the modifier may be formed in several ways. Some modifiers may be adsorbed onto the surface of graphite fibers, and cobalt phthalocyanine is exemplary.

A more universal technique involves the coating of the substrate with a composition containing the filler dispersed in a polymer matrix. Although the modifier may comprise 1-99 percent by weight of the coating composition, it will generally comprise 2-20 percent. The matrix resin formulation is conveniently one using vinyl monomers such as styrene and acrylics.

Still another technique involves the deposit on the substrate of a polymer containing the modifier in the polymer chain, generally as a branch or in some other structural position in which its functional component is available for interaction with the components of the solution in which immersed. Exemplary of suitable monomers with which modifier monomers may be copolymerized or cross-linked are vinyl monomers such as styrenes and acrylics. The modifier monomers will generally have a functional vinyl group to effect the polymerization and a modifier group.

Both types of a polymeric modifier coatings may be developed in situ upon the elongated substrates by free radical initiators or anion initiators generated electrochemically. These modifier coatings will normally have a thickness of 0.1 nanometers to 5 millimeters and preferably 0.01-10 micrometers. They will also be about 0.0005-10 times the thickness of the substrate to provide useful surface area at the tip of the microelectrode. Exemplary of such materials are vinylpyridine and vinylferrocene.

The modifier monomer will normally comprise 1-100 percent by weight of the polymerizable monomers and preferably 80-95 percent.

The distinctive properties imparted by the modifier offer the opportunity to utilize such renewable electrodes for various electrochemical applications and the properties attributable to such modifiers will be recognized by those familiar with electrochemistry and electroanalytical techniques.

Electroactivity is generally considered to be the ability to oxidize or reduce the modifier when it is disposed at the surface of an electrode in contact with a solution or other medium in which it is disposed. Such modifiers may be used as electrocatalysts, as mediators, as sources of reference potentials, and as sensors of the redox potential of the surrounding solution. Exemplary of such modifiers are cobalt phthalocyanine, polymeric species such as polyvinyl ferrocene, metal oxides such as silver oxide. Moreover, some materials may be useful as electroactive species only at certain potentials, e.g., gold amalgam, and also exhibit other desired modifier properties at other potentials.

Inclusion is generally considered to be the ability to incorporate species from the surrounding solution by ion exchange or other host-guest interactions. Such modifiers may be used as an electrocatalyst, as a support for an electrocatalyst, as a means to concentrate species from the surrounding medium, as a means of delivering species to the solution in the region surrounding the surface of the electrode, and as a potentiometric sensor for species which may be incorporated at internal or surface sites. Exemplary of such modifiers are zeolites, clays, layered double hydroxides, other layered compounds, polymeric materials with ion exchange properties, and coordinating compounds.

Adsorption is generally considered to be the ability to adsorb species from the surrounding solution by ion exchange or other surface interactions. Such modifiers may be used as electrocatalysts, as supports for electrocatalysts, as means to concentrate species from the surrounding medium, and as a potentiometric sensor for species which are adsorbed at surface sites. Exemplary of such modifiers are layered doubled hydroxides of the formula:

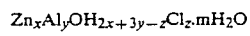

$$Zn_xAl_yOH_{2x+3y-z}Cl_z \cdot mH_2O$$

and alumina ($Al_2O_3 mH_2O$).

Electrocatalysis is generally considered to be the ability to enhance the current for oxidation or reduction of some species in solution at a given potential or current relative to a similar electrode without the modifier. Exemplary of such modifiers are layered double hydroxides which reduce the overpotential in the oxidation of catechol and related compounds. Cobalt phthalocyanine, silver oxide, zeolites and metals supported on zeolites may serve as electrocatalysts. Gold/mercury amalgams appear suitable as catalysts for thiol oxidation and disulfide reduction.

Acidic/basic is generally considered to be the ability to alter the pH of the electrode surface when immersed in the solution. Exemplary of such materials is co-poly(vinylpyridine) which can be protonated in a highly acidic solution.

Complexing/chelating is generally considered to be the ability to complex or chelate ions at the surface of the electrode when immersed in solution. Exemplary of such materials are co-poly(vinylpyridine) and monomeric forms of phenanthrolines and other coordinating or chelating ligands.

Some modifiers may exhibit properties in more than one class of activity, or different properties in different solutions or at different pH or at different applied potentials. Moreover, modified electrodes may utilize more than one type of modifier where multiple effects are desired.

The size and thickness of the electrode formed from the composition will depend upon the application, but they should be sufficient to permit its renewal by removal of the contaminated or altered surface portion of the tip. The amount of surface to be removed will depend upon the type of contamination or alteration. Generally, removal of 2–10 micrometers is required, and amounts of up to 100 micrometers may be required if the surface has been swollen by the solution. Removal of the surface may be effected by fine polishing followed by rinsing, or by slicing off surface layer, or by any other suitable technique. The electrode should then be thoroughly washed.

Such modified electrodes may have applications in various areas of technology where this surface modification improves the electrochemical activity. Electroanalysis is a particularly fertile application. Other applications include sensors and detectors. Moreover, such electrodes present an opportunity to improve apparatus using electrochemical activity such as fuel cells and batteries.

Several different methods for making the electrodes may be employed. The modifier, fluid resin composition, may be thoroughly admixed and disposed in molds or extruded under conditions which will convert the fluid resin composition into a solid matrix.

The particular technique utilized will generally depend upon the resin formulation and the modifier. Where polymerization is the principal mechanism being employed, and an initiator incorporated, admixture is generally preferable.

Following formation of the electrodes, they are desirably polished to a smooth surface. This may involve initial coarse sanding followed by polishing with a fine grit material. The surface layer could also be removed by cutting or breaking off a thin section at the tip of the electrode.

Exemplary of the present invention are the following specific examples.

EXAMPLE ONE

Single carbon fibers with a diameter of 7.2 micrometers were coated with an interpolymer by electropolymerization of vinylferrocene and technical grade divinylbenzene from a solution containing 0.5 millimolar vinylferrocene and 0.1–0.5 millimolar technical grade divinylbenzene in aqueous solution containing 60 percent dimethylacetamide and 40 percent sulfuric acid. The electropolymerization was carried out by holding the potential of the fiber at $-2$ volts versus SCE for 1–20 hours. The coating was about 20 nanometers thick. This coated fiber was coated further with commercial epoxy. When used as an electrode, the fiber showed electroactivity of the ferrocene moieties found in said coating, and also showed a signal indicating electroreduction of 3.0 millimolar hezammineruthenium(III) in aqueous solution containing 0.1 molar potassium chloride. The surface of the electrode was renewed by cutting a small slice off the tip of the fiber.

EXAMPLE TWO

An electrode was prepared as in Example Two except that the vinylferrocene was replaced by 0.5–1 millimolar vinylpyridine. Cyclic voltammetry showed that the electrode collected ferricyanide ions at its surface from acidic electrolyte solution by ion-exchange at the protonated pyridine sites.

EXAMPLE THREE

Cobalt phthalocyanine was absorbed to carbon fibers with diameters of 7.2 micrometers from about 5 millimolar by dimethyl-sulfoxide. A single fiber was prepared this way and used as a cylinder electrode in aqueous electrolyte solution. Electro activity was observed for cobalt phthalocyanine, which is a known electro catalyst.

EXAMPLE FOUR

A device was prepared that contained one fiber coated with a polymer as in Example One, and one unmodified carbon fiber. These electrodes were used as the working and pseudo reference electrodes, respectively, to observe electrochemical behavior of ferrocene on the coated fiber electrode.

Thus, it can be seen from the foregoing detailed specification and examples that the modified composite microelectrodes provide highly effective electrodes with surfaces which enhance electrochemical applications. They may be fabricated relatively easily and at relatively low cost, and they may be readily renewed by removing the contaminated or affected surface.

Having thus described the invention, what is claimed is:

1. A renewable composite microelectrode for electrochemical applications comprising:
   (a) at least one elongated conductive substrate having a cross section of less than 500 micrometers and selected from the group of conductive fibers and metallic wires, said substrate having a tip at one end thereof;
   (b) an initial surface coating extending along at least a portion of the length of said substrate from said tip and containing a modifier providing to said electrode distinctive properties selected from the group consisting of electroactivity, inclusion, adsorption, acidic/basic, complexing/chelating and electrocatalysis, said coating being a homogeneous layer of 1–99 percent by weight of a polymeric matrix and 1–99 percent by weight of said modifier dispersed therein; and
   (c) an electronically resistive polymer coating superposed thereon, said electrode at said tip of said substrate being free from said resistive coating and said initial surface coating being exposed at said tip, said electrode being renewable by removing a portion thereof at the tip of said substrate to expose a fresh portion of said initial coating at said tip.

2. The electrode in accordance with claim 1 wherein said substrate is a conductive or semiconductive fiber.

3. The electrode in accordance with claim 1 wherein said initial and resistive coatings extend over substantially the entire length of the substrate from said tip.

4. The electrode in accordance with claim 1 wherein said initial coating comprises an initial deposit of said modifier and said polymer coating is a non-conductive polymer surrounding and encapsulating a multiplicity of initially coated substrates.

5. The electrode in accordance with claim 1 wherein said modifier exhibits said distinctive such properties only upon application of a potential to said electrode.

6. The electrode in accordance with claim 1 wherein said modifier is non-conductive and enhances electroactivity upon application of a potential to the electrode in a solution.

7. The electrode in accordance with claim 1 wherein said modifier exhibiting said distinctive properties is selected from the group consisting of organic compounds and polymers.

8. The electrode in accordance with claim 1 wherein said initial coating has a thickness has a thickness of 0.1 nanometers to 5 millimeters and said resistive polymer coating has a thickness of 0.01–10 micrometers.

9. In the method of making renewable composite microelectrodes for electrochemical applications, the steps comprising:
(a) selecting an elongated conductive substrate having a cross section of less than 500 micrometers and of the group consisting of conductive fibers and wires, said substrate having a tip at one end thereof;
(b) providing an initial surface coating extending along at least a portion of the length of said substrate from said tip to form an electrode, said coating containing a modifier providing to said electrode distinctive properties selected from the group consisting of electroactivity, inclusion, adsorption, acidic/basic, complexing/chelating and electrocatalysis, said initial coating being formed by
coating said substrate with a homogeneous layer comprising a mixture of 1–99 percent by weight of a polymeric matrix and 1–99 percent by weight of said modifier dispersed therein; and
(c) superposing on said initial coating an electronically resistive polymer coating; and
(d) removing said conductive polymer at the tip of said substrate to expose said initial coating at the tip of said substrate.

10. The method in accordance with claim 9 wherein there are included the additional steps of selecting a multiplicity of microelectrodes produced in accordance with steps (a), (b), (c) and (d) of claim 9 and having different coatings exhibiting different distinctive properties, and assembling such microelectrodes into a composite electrode providing more than one of said properties.

11. The method in accordance with claim 9 wherein there are included the additional steps of:
(a) immersing said electrode in a solution to perform a function involving one of said properties; and
(b) subsequently removing a portion of said electrode at said tip of said substrate to expose fresh surface of said initial coating for further use.

12. The method in accordance with claim 9 wherein said substrate is a conductive fiber.

13. The method in accordance with claim 9 wherein said initial and resistive coatings extend over substantially the entire length of the substrate from said tip.

14. The method in accordance with claim 9 wherein said initial coating comprises an initial deposit of said modifier and said resistive polymer coating is a non-conductive polymer surrounding and encapsulating a multiplicity of initially coated substrates produced in accordance with steps (a) and (b) of claim 11.

15. The method in accordance with claim 9 wherein said modifier exhibits such properties only upon application of a potential to said electrode.

16. The method in accordance with claim 9 wherein a multiplicity of initially coated substrates is encapsulated within said electronically resistive polymer coating and step (d) is performed therafter.

17. A renewable composite microelectrode for electrochemical applications comprising:
(a) at least one elongated conductive substrate having a cross section of less than 500 micrometers and selected from the group of conductive fibers and metallic wires, said substrate having a tip at one end thereof;
(b) an initial surface coating extending along at least a portion of the length of said substrate from said tip and containing a modifier providing to said electrode distinctive properties selected from the group consisting of electroactivity, inclusion, adsorption, acidic/basic, complexing/chelating and electrocatalysis, said coating being an adsorbed layer of said modifier; and
(c) an electronically resistive polymer coating superposed thereon, said electrode at said tip of said substrate being free from said resistive coating and said initial surface coating being exposed at said tip, said electrode being renewable by removing a portion thereof at the tip of said substrate to expose a fresh portion of said initial coating at said tip.

18. The electrode in accordance with claim 17 wherein said substrate is a conductive or semiconductive fiber.

19. The electrode in accordance with claim 17 wherein said initial coating comprises an initial deposit of said modifier and said polymer coating is a non-conductive polymer surrounding and encapsulating a multiplicity of initially coated substrates.

20. The electrode in accordance with claim 17 wherein said initial coating has a thickness of 0.1 nanometers to 5 millimeters and said nresistive polymer coating has a thickness of 0.01–10 micrometers.

21. A renewable composite microelectrode for electrochemical applications comprising:
(a) at least one elongated conductive substrate having a cross section of less than 500 micrometers and selected from the group of conductive fibers and metallic wires, said substrate having a tip at one end thereof;
(b) an initial surface coating extending along at least a portion of the length of said substrate from said tip and containing a modifier providing to said electrode distinctive properties selected from the group consisting of electroactivity, inclusion, adsorption, acidic/basic, complexing/chelating and electrocatalysis, said coating being a polymer having a polymer chain containing said modifier in the polymer chain; and
(c) an electronically resistive polymer coating superposed thereon, said electrode at said tip of said substrate being free from said resistive coating and said initial surface coating being exposed at said tip, said electrode being renewable by removing a portion thereof at the tip of said substrate to expose a fresh portion of said initial coating at said tip.

22. The electrode in accordance with claim 21 wherein said substrate is a conductive or semiconductive fiber.

23. The electrode in accordance with claim 21 wherein said initial coating comprises an initial deposit of said modifier and said polymer coating is a non-conductive polymer surrounding and encapsulating a multiplicity of initially coated substrates.

24. The electrode in accordance with claim 21 wherein said initial coating has a thickness of 0.1 nanometers to 5 millimeters and said nresistive polymer coating has a thickness of 0.01–10 micrometers.

25. In the method of making renewable composite microelectrodes for electrochemical applications, the steps comprising:
(a) selecting an elongated conductive substrate having a cross section of less than 500 micrometers and of the group consisting of conductive fibers and wires, said substrate having a tip at one end thereof;
(b) providing an initial surface coating extending along at least a portion of the length of said substrate from said tip to form an electrode, said coating containing a modifier providing to said electrode distinctive properties selected from the group consisting of electroactivity, inclusion, adsorption, acidic/basic, complexing/chelating and electrocatalysis, said initial coating being formed by absorbing said modifier onto said substrate;
(c) superposing on said initial coating an electronically resistive polymer coating; and
(d) removing said conductive polymer at the tip of said substrate to expose said initial coating at the tip of said substrate.

26. The method in accordance with claim 25 wherein there are included the additional steps of selecting a multiplicity of microelectrodes produces in accordance with steps (a), (b), (c) and (d) of claim 25 and having different coatings exhibiting different distinctive properties, and assembling such microelectrodes into a composite electrode providing more than one of said properties.

27. The method in accordance with claim 25 wherein there are included the additional steps of:
(a) immersing said electrode in a solution to perform a function involving one of said properties; and
(b) subsequently removing a portion of said electrode at said tip of said substrate to expose fresh surface of said initial coating for further use.

28. The method in accordance with claim 25 wherein said initial coating comprises an initial deposit of said modifier and said resistive polymer coating is a non-conductive polymer surrounding and encapsulating a multiplicity of initially coated substrates produced in accordance with steps (a) and (b) of claim 25.

29. The method in accordance with claim 25 wherein a multiplicity of initially coated substrates is encapsulated within said electronically resistive polymer coating and step (d) is performed therafter.

30. The method of making renewable composite microelectrodes for electrochemical applications, the steps comprising:
(a) selecting an elongated conductive substrate having a cross section of less than 500 micrometers and of the group consisting of conductive fibers and wires, said substrate having a tip at one end thereof;
(b) providing an initial surface coating extending along at least a portion of the length of said substrate from said tip to form an electrode, said coating containing a modifier providing to said electrode distinctive properties selected from the group consisting of electroactivity, inclusion, adsorption, acidic/basic, complexing/chelating and electrocatalysis, said initial coating being formed by coating and substrate with a non-conductive polymer having a polymer chain containing the modifier in the polymer chain;
(c) superposing on said initial coating an electronically resistive polymer coating; and
(d) removing said conductive polymer at the tip of said substrate to expose said initial coating at the tip of said substrate.

31. The method in accordance with claim 30 wherein said initial coating comprises a non-conductive polymer having the modifier in the polymer chain, said modifier being copolymerized with a polymerizable monomer to form said non-conductive polymer.

32. The method in accordance with claim 30 wherein said initial coating comprises a non-conductive polymer having the modifier in the polymer chain, said polymer being cross-linked.

33. The method in accordance with claim 30 wherein there are included the additional steps of selecting a multiplicity of microelectrodes produced in accordance with steps (a), (b), (c) and (d) of claim 30 and having different coatings exhibiting different distinctive properties, and assembling such microelectrodes into a composite electrode providing more than one of said properties.

34. The method in accordance with claim 30 wherein there are included the additional steps of:
(a) immersing said electrode in a solution to perform a function involving one of said properties; and
(b) subsequently removing a portion of said electrode at said tip of said substrate to expose fresh surface of said initial coating for further use.

35. The method in accordance with claim 30 wherein said initial coating comprises an initial deposit of said modifier and said resistive polymer coating is a non-conductive polymer surrounding and encapsulating a multiplicity of initially coated substrates produced in accordance with steps (a) and (b) of claim 30.

36. The method in accordance with claim 30 wherein a multiplicity of initially coated substrates is encapsulated within said electronically resistive polymer coating and step (d) is performed therafter.

* * * * *